United States Patent [19]

Overhoff

[11] Patent Number: 4,899,298
[45] Date of Patent: Feb. 6, 1990

[54] HIGH RESOLUTION MEASUREMENT OF MOVING MATERIALS USING A SCINTILLATION DETECTOR

[76] Inventor: Mario W. Overhoff, c/o Overhoff Technology Corporation, 1160 U.S. Route 50, Milford, Ohio 45150

[21] Appl. No.: 160,369

[22] Filed: Feb. 25, 1988

[51] Int. Cl.⁴ .................. G06F 15/46; G01B 15/02
[52] U.S. Cl. ..................................... 364/558; 364/469; 364/472; 378/54; 378/89
[58] Field of Search .................. 364/469, 470–472, 364/527, 558, 563; 378/54–56, 58, 89; 250/358.1, 359.1, 360.1, 370.11

[56] References Cited

U.S. PATENT DOCUMENTS

| | | | |
|---|---|---|---|
| 4,156,913 | 5/1979 | Apicella | 364/469 |
| 4,331,241 | 5/1982 | Smirin et al. | 378/54 |
| 4,423,327 | 12/1983 | Alexander | 378/54 |
| 4,514,812 | 4/1985 | Miller et al. | 364/469 |
| 4,549,306 | 10/1985 | Shideler et al. | 378/56 |
| 4,575,808 | 3/1986 | Kaneko | 364/558 |
| 4,633,420 | 12/1986 | Masanobu | 364/469 |
| 4,734,922 | 3/1988 | Harris | 378/55 |

Primary Examiner—Parshotam S. Lall
Assistant Examiner—Kevin J. Teska
Attorney, Agent, or Firm—Biebel, French & Nauman

[57] ABSTRACT

A method and apparatus for detecting and measuring the areal density of a moving sheet of material having a repetitive pattern by using a scintillation detector operating either in the pulse counting mode or as an analog device includes some means for determining the duration of the repetitive pattern. If the repetition is caused by some characteristic of the production machine, a sensor or pickoff device may be used to synchronize the process; otherwise, the lowest frequency component of a Fourier transform of the variations in areal density is used to determine the repetition interval. Each repetition interval is divided into small measurement increments, and means are employed to average the output of the scintillation detector for each of the corresponding measurement increments in order to provide an accurate and high resolution measurement throughout the repetition interval using an otherwise limited detection device.

12 Claims, 3 Drawing Sheets

HIGH RESOLUTION MEASUREMENT OF MOVING MATERIALS USING A SCINTILLATION DETECTOR

BACKGROUND OF THE INVENTION

This invention relates to a method and apparatus for detecting and measuring repetitive patterns of nonuniformities in film or sheet materials such as paper, plastics or foil products using nuclear gauging devices.

Nuclear (beta ray) gauges have been used since the early 1950's for the measurement of sheet or film products such as paper or plastic or metal foils. Such measurements are of great value to the manufacturing industry since the gauges can be used to measure and process control while the product is being fabricated.

Nuclear gauges operate by detecting the nuclear radiation emitted by a source after passage through the material to be measured. Since radiation is partially absorbed by the material to be measured, it is possible to relate the thickness (or areal density) of the material to the degree to which the radiation has been absorbed or attenuated during passage. The thicker the material, the greater is the attenuation of the transmitted radiation.

It is also common to make such measurements by means of measuring radiation that has been scattered or reflected from the material to be measured, rather than transmitted. Using this technique, the detected radiation increases with increasing thicknesses. In either case, the change in the detected radiation with change in the thickness of the material being measured is usually approximated by an exponential function.

Nuclear radiation is radiation emitted when an atom disintegrates spontaneously, ejecting either a photon (gamma or X-rays) or a particle (alpha, beta or neutrons). Often, more than one form of radiation is emitted from any given source.

In all cases, the disintegration process (radioactivity) is purely a random phenomenon, it is not constant, but is statistical in nature. In fact, nuclear radiation follows a Poisson distribution, and when detected with sufficient sensitivity, it is seen to be quite random or noisy in character. The radiation is emitted in discrete pulses, irrespective of the particular physical form (alpha, beta, gamma or neutron). For a Poisson distribution, the mean statistical deviation is the square root of the number of events, and is quite easy to calculate when the detected transmitted (reflected) radiation is known. The normalized statistical deviation, or practically speaking, the noise observed at the detector, is thus related to the reciprocal square root of the source strength, as well as the reciprocal of the square root of the duration of measurement. Or, more simply put, to the reciprocal square root of the radiation events (disintegration) actually measured.

Since nuclear radiation is generally considered to be dangerous to one's health, it is not surprising to find that radiation levels in most nuclear gauging applications are so weak as to show well pronounced noise. In order to make sensitive measurements, it is therefore necessary to take the measurements over appreciable lengths of time, or in other words, to employ long measuring time constants. Quite evidently, a compromise is made between measurement sensitivity and measurement time constant or the response rate of a nuclear gauge.

Beta gauges, as used today, have typical time constants of a tenth of a second. To obtain measurements of high resolution, the gauging signals may be subjected to averaging with equivalent time constants of up to ten seconds or more. For relatively coarse measurements, time constants as short as 10 milliseconds have been used.

Products, such as paper, are made on high speed machinery, and production speeds of 3000 feet per minute are not uncommon, a line speed of 50 feet per second or 0.6 inches per millisecond. To make real time measurements using nuclear gauges with any degree of precision over distances of inches or less is therefore apparently not possible, at least not by conventional techniques.

The gauge response rate is also determined by the response rate of the detectors used and to some degree, the associated electronics. The detector predominantly used today is the ionization chamber, which is inherently a slow device. Less commonly used is the detector comprising a scintillator - photomultiplier combination. This type of detector can be operated in either of two modes. The simpler mode is to use the detector in an analog or DC current mode. The second mode is to use the detector as an event or pulse counter. The earliest beta gauges was an event counting scintilator photomultiplier. That device proved totally impractical at the time (early 1950's) due to the lack of fast electronic counters. The scintillation counter was replaced in the 1950's by the ionization chamber, and later by the analog scintillation detector.

The scintillation detector, in either the DC or in the event counting mode, is extremely fast when compared to the ionization chamber, and unlike the ionization chamber may, in principle, be used for fast gauging.

SUMMARY OF THE INVENTION

This invention relates to the use of a scintillation detector, particularly in the pulse counting mode, in the measurement of rapidly varying product, such as paper and the like, during production Although it would appear that high measurement precision or resolution and speed are at first glance mutually exclusive, this invention nevertheless permits high resolution measurements to be made on rapidly moving materials by taking measurements at regular intervals using a scintillation detector and averaging the corresponding measurements in the period repetition of the variations.

This general principle has been used in the so-called sampling oscilloscope where the method is used to display a signal whose frequency components vastly exceed the frequency capabilities of the basic major sections of the oscilloscope being used, but it has never been used to improve the performance of nuclear gauges.

By applying this technique to the output of a scintillation detector, which is a relatively slow device, high resolution measurements that were heretofore unattainable by using this type of radiation gauge, may now be made.

Accordingly, it is an object of this invention to provide a method of measuring the areal density of an article wherein there are periodic repetitions of the areal density variations comprising the steps of causing relative movement between the scintillation detector and the article, sensing the areal density at regular intervals, which intervals define the measurement increment, repeating the measurements within each periodic increment at the same relative position within the periodic repetition cycle, and averaging the measurements taken within each of the increments over a plurality of measurement cycles to obtain a high resolution and accurate measurement of the variations throughout the material.

It is also an object of this invention to provide a nuclear gauging apparatus for obtaining a high resolution measurement of the areal density of a moving article wherein there are periodic repetitions of the areal density, comprising a scintillation detector, means for causing relative movement between said detector and the article, means for sensing the areal density by the scintillation detector at regular intervals, which intervals define a measurement increment, means for determining the interval in which the periodic repetition occurs, and means for averaging a plurality of measurements taken within corresponding increments within the periodic repetition interval to obtain an accurate measurement of the areal density of the article.

Other objects and advantages of the invention will be apparent from the following description, the accompanying drawings and the appended claims.

DESCRIPTION OF THE INVENTION

Figure 1:
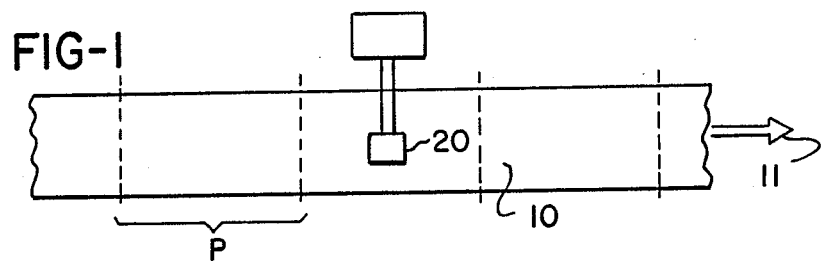
FIG. 1 is a plan view showing a moving sheet having a periodic repetition cycle of length P, with the areal density of the sheet being measured by a scintillation detector.

Referring now to the drawings which illustrate a preferred embodiment of the invention, and particularly to FIG. 1, a sheet of material 10 is shown moving in the direction of the arrow 11. The material 10 has, for whatever reason, variations in its density along the direction of movement which are periodically repeated. The duration of the pattern is represented by P, and in FIG. 1, three such repetitions are show. A beta gauge 20 including a radiation source 21 and scintillation detector 22 is placed adjacent the sheet of material 10 to measure the variations in thickness or areal density along the direction of movement, as will be explained.

Figure 2:
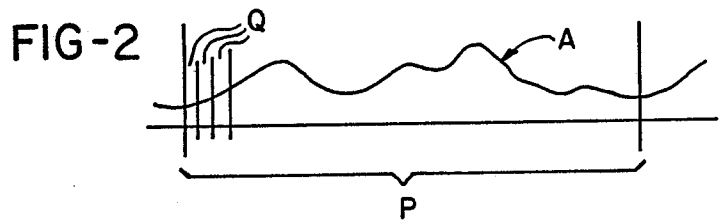
FIG. 2 is a chart showing the average variation in areal density throughout one periodic interval.
Figure 3A:
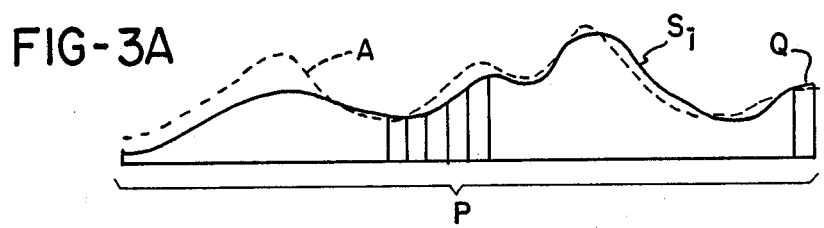
FIGS. 3A-3E are charts showing the variations in areal density over a plurality of measurement cycles.
Figure 3B:
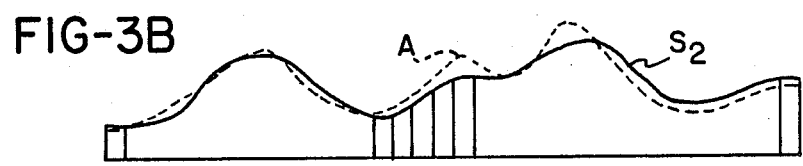
Figure 3C:
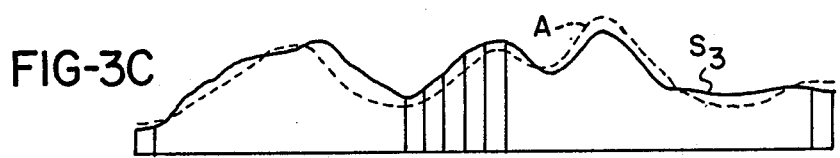
Figure 3D:
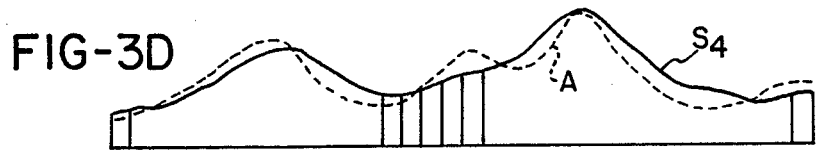
Figure 3E:
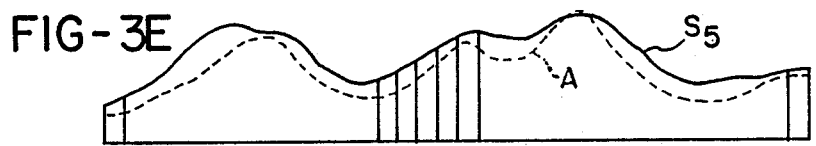

FIG. 2 represents the average variations A in the areal density during the repetition interval P. The average is a result of multiple measurements taken in the smaller measurement increments. The smallest measurement increment possible is, as will be explained, a function of the resolution that is possible from the scintillation detector. Obviously, the higher the resolution, the more accurately the variations in areal density can be determined.

FIGS. 3A-3E show a set of measurements taken over five different repetition intervals P. As shown in this set of curves, the density exhibits slight random variations from interval to interval. The average of all the scans is shown by the dotted line A while the actual measurement for a particular scan is represented by the solid lines S1-S5.

Each scan interval is segmented into discrete samples (data points), the number of samples per scan can be chosen at will. If there are Q discrete measurement increments or samples for each measurement cycle or repetition interval of duration of P seconds, then the sampled data averaging process consists of averaging all i'th samples of Q for, say, S number of scans.

If $M_{ij}$ is the data measurement for the i'th increment or sample in the j'th measurement, then the sampled data measurement average for the i'th sample point is expressed as;

$$A_i = \frac{1}{S} \sum_{j=1}^{S} M_{ij}$$

It will be noted that the effective time (duration of the sample data average) (T) is equal to the product of the time duration of each sample (P/Q) and the number of scans (S) taken.

$$T = S \frac{P}{Q}$$

Thus, T is the sampling time and is a quantity of interest when considering the basic random noise associated with the nuclear measurement as mentioned above.

The sample averaging time is increased by increasing the number of scans over which the averaging takes place, but is reduced as the duration of each sample is reduced (as the number of samples per scan is increased). Obviously, increasing the sampling time T has the benefit of providing a more accurate sampled data measurement, while increasing the number of data points Q will improve the image resolution.

The actual averaging method actually used in practice may differ slightly from the simplified version described above, but the end result, as far as practical performance is concerned, still remains the same. The chief difference lies in the fact that sample data averaging is not performed over a fixed number of S scans, but that the process of averaging is continuous in time. In equation (1), the average value Ai is obtained by summation of all measurement values $M_{ij}$ equally weighed. In actual practice, the averaging is done by running method where the most recent sampled data measurement is fully weighed, but earlier measurement values are progressively less weighed as they become older.

It should also be noted that it is obviously possible to perform several separate signal processing schemes concurrently. It is thus possible to make conventional measurements concurrently with one or more sampled data averaging measurements.

By way of illustration, one typical application is for production measurement on a paper machine. By using concurrent signal processing, the basis weight of the paper can be measured in "real time" and the measurement signal used for data display or for process control or information gathering. Simultaneously, one can perform sampled data averaging in order to search for possible non-uniformities that may be due to wet spots, machine irregularities, such as uneven rollers, flutter at the head box, or any other such periodically repeated flaw. With sufficient sampling speed, it is even possible to analyze for "furnish" of the paper. These operations can also be performed with scanning gauges where the gauge is made to traverse back and forth across a web of paper or other process product.

Other applications include making measurements when the pattern is not a flaw or defect to be searched for, but when the pattern is intentional. A typical example might be the measurement of adhesive coatings that are added in the form of striations. Other examples are measurements of patterned laminates, of perforation patterns or other intentionally introduced repetitive patterns.

Of paramount importance when sample averaging is, quite obviously, that the averaging is performed on truly properly corresponding points in each consecutive scan. This indicates that the pattern duration or repetition rate is accurately known, and that sample scans can be synchronized.

Patterns that are not truly stationary, ones that may vary in time, may pose limits to the sample data averaging process by restricting measurement resolution in one form or another. If, for example, the duration of the repetitive pattern is slightly out of synchronization with the measurement scan rate, then the data display of the sample average will be seen to "walk" or to jitter. In any event, in order to make measurements by sampled data averaging of repetitive patterns, it is axiomatic that this requires knowledge of the pattern duration or the scan time may also be a multiple of the pattern duration; it results in the display of several of the patterns one after the other.

A knowledge of the pattern repetition rate can either be predicated on assumptions relating to the physical parameters of the measurement, or it can be based upon the results of an arbitrary search. An example of the first instance might take the form of determining flaws in the product when the flaw can be assumed to be related to the rollers in the paper machine. Here, one simply sets the scan length of the sample data process to equal the duration of the revolution of the roller in question. In fact, one can use any kind of pick-off or strobotachymetric means for synchronization.

If, however, there is no a prior index for selection of a suitable scanning period or repetition rate, then it must be provided to make an open-ended search. One method for doing this would be to use the gauge in its conventional but ultra fast measurement mode, and taking the Fourier transform of the measurement over a period of time sufficient to show a transform pattern. The lowest frequency component of the Fourier transform would then be used to establish the scan for the sampled data averaging.

Figure 4:
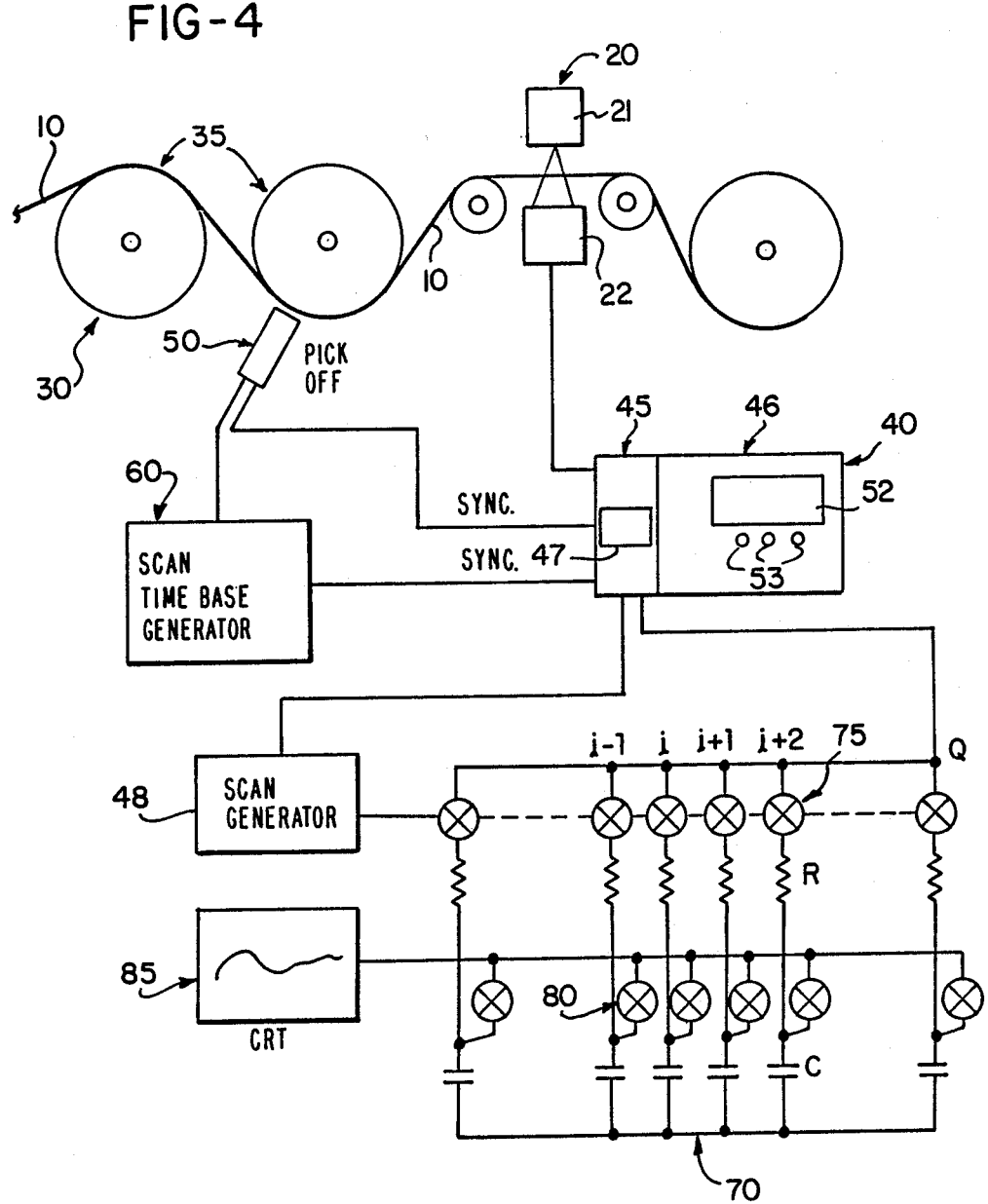
FIG. 4 illustrates one embodiment of the invention and shows a scintillation detector associated with a production machine, wherein the output of the scintillation detector is applied to an analog analyzing circuit.
Figure 5:
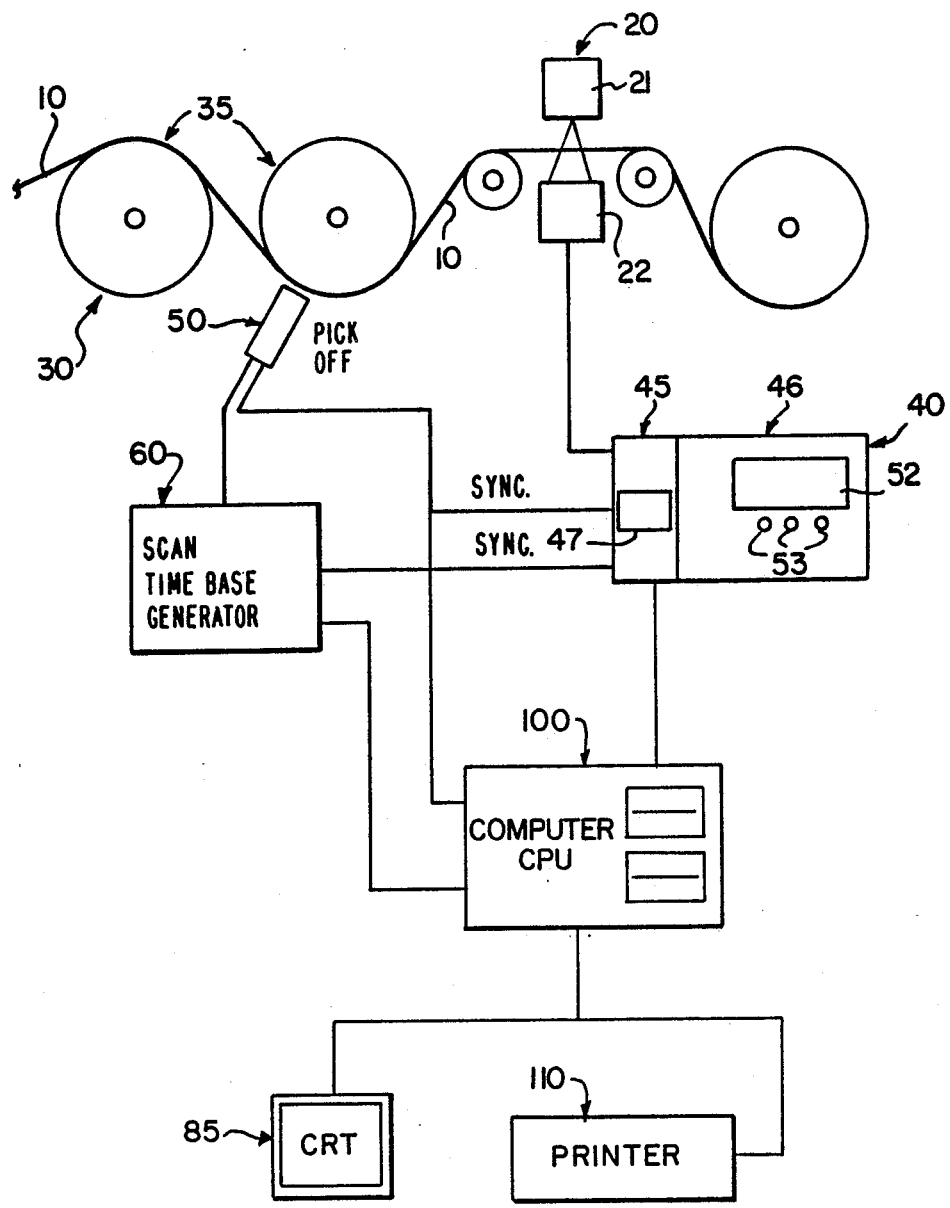
FIG. 5 is a view showing a scintillation detector associated with a production machine, with the output of the scintillation detector being applied to a digital analysis circuit.

FIGS. 4 and 5 show a scintillation beta gauge or detector 20 placed adjacent the output of a production machine 30 for paper, plastics or any other sheet product material. The machine is depicted as consisting of rollers 35 which support the product 10 being fabricated.

Signals from the scintillation detector 22 are brought to a central electronics package 40 which includes a sampling unit 45 and a signal processing unit 46. This is a conventional processing unit for averaging and scaling the output of the counter 22 and provides a display 52 indicating the average value of the areal density of the material 10. For example, in conventional gauges, this would have a time constant of from one-tenth to 10 seconds, or whatever is suitable for a given application. Controls 53 select the zero, span and the time constant so that the display represents areal density in suitably chosen engineering units. The sampling duration, previously designated as P/Q seconds, can be selected manually at the sampling unit by means of thumbwheel switches 47 which in turn control the frequency of a scan generator 48.

In order to provide scan start (or repeat) signals, either of two methods may be used. In the first instance, when scanning is synchronized to the fabrication machine, a simple pick-off 50 of any suitable form can be attached to the machine. In the second instance, after determining the basic repetition rate by means of Fourier transforms, the scanning start signals are derived from a highly stable continuously adjustable time base generator 60.

In either case, whether scan start is derived from a pick-off device 50 or derived from a time base generator 60, a scan start signal is used to synchronize precisely the sampled signals from the sampling unit 45. Obviously, if the appropriate data samples do not correspond in time from scan to scan, it is not possible to obtain correct averaging. For this reason the sampling unit can be synchronized from either the machine pick off or the time base generator.

After triggering, the sampling unit 45 will free run, producing Q samples for a period of time P. It can be noted that it is neither sufficient nor necessary that P is an integral number of Q. That is to say that the last time portion, just at the end of the period P need not be a whole P/Q, but can be a fraction thereof. In this case, the last piece of measurement, namely, the fractioned signal, is simply discarded.

The output sampled data signals from the sampling unit 45 are now averaged in the computing section. This can be implemented in either an analog form, as shown in FIG. 4, or in a digital computer form, as shown in FIG. 5.

Referring to FIG. 4, the sampled data output from the sampling unit 45 are impressed onto a plurality of R-C networks shown generally at 70. Since there are Q sample increments per measurement interval or scan, there are to be Q R-C networks, one R-C network for each "i" data sample point.

Multiplexing switches 75 are operated under control of the scan generator 48 to ensure that samples are correctly fed to the appropriate R-C network, scan after scan.

Multiplexing switches 80, also under control of the scan generator 48, are used to connect the signal on each capacitor to a cathode ray tube display circuit 85 to display the sampled data average, where the average now also has a linear time constant of RCP/Q seconds.

To change this time constant, it is necessary to physically change the values of all the resistors, of all the capacitors. This may be inconvenient, except for permanent fixed applications. Therefore, it may be more expedient to use a digital computer as shown in FIG. 5.

When using a digital computer, the sampled data measurements from the sampling unit 45 are stored in separate registers (Q registers) in the computer 100. The sampled data are sorted by timing signals from the sampling unit 45, and, for scan start, by a synchronization signal from the machine pick-off 50, or from the scan time base generator 60. The data information in each of the Q registers is now averaged over time, and the contents of each register can be read and displayed on a CRT display 85. This display is, once again, the sampled data average.

The sampled data average can, of course, also be printed out on a printer 110, or otherwise used for control or display purposes.

Averaging can be performed in many ways, and is mainly dependent upon the size and speed of the computer used and the complexity of the program to be written. For example, it is possible to add all corresponding data to each register and divide by the number of scans to arrive at a totalized sample average. No doubt most computers would soon run out of storage, and this method, while straightforward, is not practical.

Among many that are possible, there are two averaging methods that are directly usable. The first method is to store each of the corresponding "i" data in a FIFO register, and averaging the contents. In this way, one obtains the sampled data average of the last S scans, the FIFO having a length of S places.

A second method, which has the virtue of providing a time constant somewhat similar to that of an analog linear time constant, is as follows: the data are averaged in Q registers by progressively updating the sampled average as follows:

$A_{ij}$ = the previously calculated sample average for the i'th register on the j'th scan, $M_{i,j+1}$ = the data measurement (sample) for the i'th point or register on the following scan (j+1).

The next calculated (running) average for the j+1 'th scan, is therefore given by:

$$A_{i,j+1} = [A_{i,j} \times (N-1)/N] + M_{i,j+1}/N$$

While the method herein described, and the form of apparatus for carrying this method into effect, constitutes a preferred embodiment of this invention, it is to be understood that the invention is not limited to this precise method and form of apparatus, and that changes may be made in either without departing from the scope of the invention, which is defined in the appended claims.

What is claimed is:

1. A method of using a scintillation detector to measure the areal density of an article wherein there are periodic repetitions of the areal density, the method comprising the steps of
    causing relative movement between said detector and the article,
    measuring the areal density by the scintillation detector at regular intervals, which intervals define a measurement increment,
    repeating the measurements within each measurement increment at the same relative position within the periodic repetition, and
    averaging the measurements taken within each increment over a plurality of periodic repetition intervals to obtain an accurate measurement of the areal density of the article.

2. The method of claim 1 wherein the article is repeatedly scanned over the same surface in order to obtain the plurality of measurement cycles.

3. The method of claim 1 wherein the article is moving linearly relative to said detector and wherein the period of the variations in the areal density of the article is related to a moving component of a device moving the article.

4. The method of claim 1 wherein the article is moving linearly relative to said detector, the method further including the step of determining the period of variations in the areal density of the article based on a Fourier analysis of the variations in areal density being detected.

5. The method of claim 1 further including the step of simultaneously calculating and displaying the average value of the areal density.

6. A method of using a scintillation detector having a relatively slow response time to measure the areal density of a rapidly moving article of a type having periodic repetitions in its areal density, the method comprising the steps of
    positioning the scintillation detector to measure the areal density of the article as it moves past the detector,
    measuring the areal density at specified measurement increments within the periodic repetition by the scintillation detector,
    repeating the measurements within each measurement increment at the same relative position within the periodic repetition, and
    averaging the measurements taken within each increment over a plurality of periodic repetition intervals to obtain an accurate measurement of the areal density of the article.

7. A nuclear gauging apparatus for obtaining a high resolution measurement of the areal density of a moving article wherein there are periodic repetitions of the areal density, the gauging apparatus comprising
    a scintillation detector,
    means for causing relative movement between said detector and the article,
    means for measuring the areal density by the scintillation detector at regular intervals, which intervals define a measurement increment,
    means for determining the interval in which the periodic repetition occurs, and
    means for averaging a plurality of measurements taken within corresponding increments within the periodic repetition interval to obtain an accurate measurement of the areal density of the article.

8. The apparatus of claim 7 wherein said means for determining the periodic repetition interval includes means for sensing the lowest frequency component of a Fourier transform taken of the output of the scintillation detector.

9. The apparatus of claim 7 wherein said means for determining the periodic repetition interval includes means associated with equipment used to produce the article for sensing the movement of that component which produces the periodic variation.

10. The apparatus of claim 7 wherein said scintillation detector is an analog device.

11. The apparatus of claim 7 wherein said scintillation detector is a pulse counting device.

12. The apparatus of claim 7 further including means for simultaneously calculating and displaying the average value of the areal density.

* * * * *